United States Patent
Degrave et al.

(10) Patent No.: US 10,905,648 B2
(45) Date of Patent: Feb. 2, 2021

(54) **COMPOSITION COMPRISING AN EXTRACT OF LEAVES OF THE *LANSIUM DOMESTICUM* PLANT AND METHODS OF USE FOR DEPIGMENTATION OF THE SKIN AND/OR SKIN APPENDAGES**

(71) Applicant: BASF BEAUTY CARE SOLUTIONS FRANCE SAS, Lyons (FR)

(72) Inventors: Véronique Degrave, Tassin-la-Demi-Lune (FR); Corinne Reymermier, Charly (FR)

(73) Assignee: BASF BEAUTY CARE SOLUTIONS FRANCE SAS, Lyons (FR)

( * ) Notice: Subject to any disclaimer, the term of this patent is extended or adjusted under 35 U.S.C. 154(b) by 0 days.

(21) Appl. No.: 16/461,931

(22) PCT Filed: Nov. 16, 2017

(86) PCT No.: PCT/FR2017/053129
§ 371 (c)(1),
(2) Date: May 17, 2019

(87) PCT Pub. No.: WO2018/091825
PCT Pub. Date: May 24, 2018

(65) Prior Publication Data
US 2019/0321284 A1 Oct. 24, 2019

(30) Foreign Application Priority Data
Nov. 17, 2016 (FR) ...................................... 16 61162

(51) Int. Cl.
*A61K 36/58* (2006.01)
*A61K 8/9789* (2017.01)
*A23L 33/105* (2016.01)
*A61Q 19/02* (2006.01)
*A61K 9/00* (2006.01)

(52) U.S. Cl.
CPC .......... *A61K 8/9789* (2017.08); *A23L 33/105* (2016.08); *A61K 36/58* (2013.01); *A61Q 19/02* (2013.01); *A61K 9/0014* (2013.01); *A61K 9/0053* (2013.01); *A61K 2236/333* (2013.01)

(58) Field of Classification Search
None
See application file for complete search history.

(56) References Cited

U.S. PATENT DOCUMENTS

| 8,906,425 B2 | 12/2014 | Perrier et al. |
| 2004/0096925 A1 | 5/2004 | Perrier et al. |
| 2004/0180033 A1 | 9/2004 | Msika |
| 2007/0184012 A1 | 8/2007 | Perrier et al. |
| 2011/0052739 A1 | 3/2011 | Rival et al. |

FOREIGN PATENT DOCUMENTS

| EP | 1119344 A1 | 8/2001 |
| FR | 2847267 A1 | 5/2004 |
| FR | 2855968 A1 | 12/2004 |
| FR | 2893252 A1 | 5/2007 |
| FR | 2929511 A1 | 10/2009 |
| JP | S63215611 A | 9/1988 |
| JP | 2001122731 A | 5/2001 |
| WO | WO-00/19974 A1 | 4/2000 |
| WO | WO-2005/120554 A1 | 12/2005 |

OTHER PUBLICATIONS

Nishizawa, M. et al. Isolation of a New Cycloartanoid Triterpene from Leaves of Lansium domesticum. Tetrahedron Letters 30(41)5615-18, 1989. (Year: 1989).*
Tillaar M. et al. Review of Lansium domesticum Correa and its Use in Cosmetics. Boletin Latinoamericano Y del Caribe de Plants Medicinales y Aromaticas. 7(4)183-189 Jul. 2008. (Year: 2008).*
Matsumoto T. et al. Structures and Antimutagenic Effects of Onoceranoid Type Triterpenoids from the Leaves of Lansium domesticum. J of Natural Products 81(10)2187-2194, 2018. (Year: 2018).*
Mochamad L. et al. Determination of Progesterone Compounds in the Crude Methanol Extract of Benalu Duku Leaves. Veterinary World 12(3)58-366, 2019. (Year: 2019).*
Arung, E. T., et al., "Evaluation of Medicinal Plants from Central Kalimantan for Antimelanogenesis", Journal of Natural Medicines, 2009, vol. 63, No. 4, pp. 473-480.
Tilaar, M., et al., "Review of *Lansium domesticum* Corrêa and its Use in Cosmetics", Boletin Latinoamericano y del Caribe de Plantas Medicinales y Aromáticas, 2008, vol. 7, No. 4, pp. 183-189.
Yapp, D. T. T., et al., "*Lansium domesticum*: Skin and Leaf Extracts of this Fruit Tree Interrupt the Lifecycle of *Plasmodium falciparum*, and Are Active towards a Chloroquine-Resistant Strain of the Parasite (T9) in vitro", Journal of Ethnopharmacology, 2003, vol. 85, No. 1, pp. 145-150.
International Search Report for PCT/FR2017/053129 dated Mar. 9, 2018 with English Translation Attached.
International Preliminary Report on Patentability for PCT/FR2017/053129 dated Mar. 9, 2018.

* cited by examiner

*Primary Examiner* — Ralph J Gitomer
(74) *Attorney, Agent, or Firm* — Faegre Drinker Biddle & Reath LLP

(57) ABSTRACT

The present disclosure describes a *Lansium domesticum* leaf extract and methods of using the leaf extract for decreasing the pigmentation of the skin and/or of the skin appendages, and/or decreasing the pigment spots on the skin. The disclosure further describes methods of using the leaf extract for the treatment of pathological conditions involving a pigment dysregulation. The disclosure also describes cosmetic compositions and pharmaceutical compositions comprising the leaf extract.

20 Claims, No Drawings
Specification includes a Sequence Listing.

```
SEQUENCE LISTING

<160> NUMBER OF SEQ ID NOS: 2

<210> SEQ ID NO 1
<211> LENGTH: 128
<212> TYPE: RNA
<213> ORGANISM: Homo sapiens

<400> SEQUENCE: 1
uggaggccuu gcugguuugg aaaguucauu guucgacacc auggaucucc agguggguca      60
aguuuagaga ugcaccaacc uggaggacuc caugcuguug agcuguucac aagcagcgga     120
cacuucca                                                             128

<210> SEQ ID NO 2
<211> LENGTH: 22
<212> TYPE: RNA
<213> ORGANISM: Homo sapiens

<400> SEQUENCE: 2
caaccuggag gacuccaugc ug                                              22
```

COMPOSITION COMPRISING AN EXTRACT OF LEAVES OF THE *LANSIUM DOMESTICUM* PLANT AND METHODS OF USE FOR DEPIGMENTATION OF THE SKIN AND/OR SKIN APPENDAGES

RELATED APPLICATIONS

This application is a national stage application (under 35 U.S.C. § 371) of PCT/FR2017/053129, filed Nov. 16, 2017, which claims benefit of French Application No. 1661162, filed Nov. 17, 2016.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_220705_0001. The size of the text file is 1 KB, and the text file was created on May 16, 2019.

The subject of the present invention is the cosmetic and/or nutraceutical or pharmaceutical, preferentially dermatological, use of a plant extract for decreasing the pigmentation of the skin and/or of the skin appendages, and/or decreasing pigment spots, and/or for treating and/or preventing hyperpigmentation of the skin and/or of the skin appendages.

The skin pigmentation process, also known as "melanogenesis", comprises numerous steps ranging from melanin synthesis in the melanocytes to the transport of said melanin into the keratinocytes of the epidermis by means of the melanosomes. Several proteins are involved in this process. Tyrosinase (TYR) is the first enzyme responsible for melanin synthesis and cooperates with two other proteins, known as TYR-related protein 1 (TYRP1) and dopachrome tautomerase (TYRP2) to convert the melanin into eumelanin and pheomelanin.

In addition, during skin ageing, in particular under the effect of radiation, typically ultraviolet radiation, brown spots, termed senile or pigment spots, also known as age spots, can appear, characterizing an acceleration of melanogenesis, often judged to be unaesthetic.

There is a growing need in the cosmetics field for the development of active ingredients capable of depigmenting the skin for aesthetic reasons, in particular in certain regions of the world such as Asia, within a population which is more subject to pigment spots. This need is all the greater since the known depigmenting cosmetic active agents are predominantly chemical molecules, the efficacy and innocuousness of which are sometimes questionable. Moreover, most of the active agents available on the market reduce melanogenesis via an effect of direct inhibition of the tyrosinase activity. Thus, the main drawback of such active agents is that they have a short-term effect since, in their absence, when their application is stopped or slowed down, the protein that is present becomes active again and resumes at the same level of activity as initially. Such active agents therefore have no long-term effect. There is a high demand in the cosmetics industry for the development of natural plant active agents with a long-lasting effect.

The inventors have discovered, surprisingly, that an extract of leaves of the *Lansium domesticum* plant has the capacity to decrease the pigmentation of the skin and/or of the skin appendages, in particular by decreasing melanogenesis, most particularly by an increase in the genic expression of miRNA490, making this extract an alternative ingredient of interest in the cosmetics industry corresponding to the problem to be solved, in particular by virtue of its long-lasting effect.

The *Lansium domesticum* plant is a tree of the family Meliaceae originating from South East Asia, that is found in Thailand, Indonesia and Vietnam, but also in Australia, India and Sri Lanka, and also in certain islands of Central America.

The plant is known to be a medicinal plant. The skin of the fruit, which is difficult to separate from the fruit, is rich is oleoresin and is used against intestinal spasms. The ground seeds are used for treating fever and the bark is used for treating malaria. The fruit is known in the cosmetics industry. Thus, a pericarpe extract has been used in a composition as an anti-acne agent (JP19870046320). Patent application JP2001122731 discloses, moreover, an *L. domesticum* extract in a cosmetic composition as a skin-moisturizing agent. The fruit is also known as a depigmenting active agent via its anti-tyrosinase and antioxidant activity (Tilaar M T., Review of *Lansium domesticum* Corrêa and its use in cosmetics, 2007, Boletin Latinoamericano y del Caribe de Plantas Medicinales y Aromaticas, 7, pages 183 to 189). A methanolic extract of *L. domesticum* bark has also shown its ability to inhibit melanin synthesis via its anti-tyrosinase effect (L-DOPA and tyrosinase from fungus) and inhibition of melanin synthesis in B16 melanocytes (Arung E T., Evaluation of medicinal plants from Central Kalimantan for antimelanogenesis, 2009, J. Nat. Med., 63, pages 473 to 780).

However, to the applicant's knowledge, no cosmetic use of *L. domesticum* leaves as a depigmenting agent has been descried in particular for a long-lasting effect. The present invention offers the advantage of supplying an effective depigmenting active ingredient which is an alternative to those that are already known. This novel ingredient is, moreover, extracted from a non-toxic plant, is easy to formulate and can be produced on an industrial scale. In addition, said leaf extract has the considerable advantage of increasing the gene expression of miRNA490 which, contrary to tyrosinase activity inhibitors, makes it possible to obtain a long-lasting effect. This makes it possible to also reduce over time the amount and/or the frequency of applications of the active agent. Finally, in so far as it is a leaf extract, the present invention offers the advantage of a raw material that is available throughout the year and in a large amount, which falls within an approach of sustainable development through the use of a renewable raw material.

A first subject of the invention therefore relates to the cosmetic and/or nutraceutical use of a *Lansium domesticum* leaf extract for decreasing the pigmentation of the skin and/or of the skin appendages, preferentially of the hair and body hair, and/or for decreasing brown spots on the skin.

The expression "cosmetic and/or nutraceutical use" is intended to mean herein a non-therapeutic, non-pharmaceutical use, that is to say a use intended for any area of skin and/or skin appendage referred to as healthy.

The expression "area of healthy skin" is intended to mean an area of skin on which the extract according to the invention is applied, termed "non-pathological" by a dermatologist, also described as "normal", that is to say which does not show any infection, scar, skin disease or ailment such as candidiasis, impetigo, psoriasis, eczema, acne or dermatitis, or any wounds or injuries and/or other dermatoses.

The extract is intended to be applied to all or part of the body chosen from the hands, the neck, the neckline, the stomach, the arms, the thighs, the hips, the waist and/or the face, and/or the skin appendages, and preferentially the hands, the neck, the neckline and/or the face, more preferentially the face.

The term "skin appendages" is intended to mean the hair, the body hair, the nails, preferentially the hair and/or the body hair, more preferentially the body hair.

For the purposes of the present invention, the expression "decreasing in the pigmentation of the skin and/or of the skin appendages" is intended to mean decreasing the amount of melanin by at least 50%, preferentially by at least 75%, more preferentially by at least 85% in the presence of the *L. domesticum* extract according to the invention, relative to the amount of melanin measured in the absence of the extract. The amount of melanin can be measured according to the techniques known by those skilled in the art, such as for example in B16 melanocytes, in particular in the presence of the *L. domesticum* extract such as that prepared according to example 1a), under the conditions described in example 5. In one advantageous embodiment of the invention, the measurement is carried out by measuring the optical density at 475 nm.

According to one advantageous mode, the decrease in the pigmentation is long-lasting, that is to say that the level of pigmentation after application of the extract according to the invention is maintained for at least two days, preferentially at least four days after the use of the extract according to the invention has been stopped.

In one particularly advantageous embodiment of the invention, the extract according to the invention increases the expression of miRNA490, which is also known as hsa-mir-490, and defined in the mribase.org reference base under the reference MI0003125 and has a pre-mature sequence of SEQ ID No 1: UGGAGGCCUUGCUGGUU-UGGAAAGUUCAUUGUUCGAGACCAUGGAUCU CC-AGGUGGGUCAAGUUUAGAGAUGCACCAACCUGG-AGGACUCCAUGCUGUUGAGCUGUUCACAAGCAG-CGGACACUUCCA). The mature miRNA is hsa-miR-490-3p of SEQ ID No 2: CAACCUGGAGGACUCCAUGCUG. The expression "Increasing the expression of miRNA490" is intended to mean increasing the gene expression of miRNA490. The increase in the expression of miRNA490 is by at least 1%, preferentially by at least 25%, more preferentially by at least 40% in the presence of the *L. domesticum* extract according to the invention, relative to the level of expression detected in the absence of the extract. Advantageously, the expression of miRNA490 is measured in melanocytes, advantageously human melanocytes that are termed normal, that is to say non-pathological. Again advantageously, the increase in the expression of miRNA490 is measured by RT-PCR, again advantageously in the presence or absence of the *L. domesticum* extract prepared according to example 1a), under the conditions described in example 4.

In one particularly advantageous embodiment of the invention, the extract according to the invention decreases the tyrosinase (TYR) gene and/or protein expression. According to the invention, the expression "decreasing the tyrosinase (TYR) gene and/or protein expression" is intended to mean causing a decrease of at least 15%, preferentially of at least 25%, more preferentially of at least 37% of the TYR expression in the presence of the *L. domesticum* extract according to the invention, relative to the level of expression measured in the absence of the extract. Preferentially, it is a decrease in the TYR protein expression. Again advantageously, the measurement of the protein expression is carried out in human melanocytes termed normal, more preferentially by Western blot, more preferentially in the presence of the *L. domesticum* extract prepared according to example 1a), under the conditions described in example 3.

Various in vivo measurement techniques can also be used to measure the decrease in pigmentation of the skin and/or of the skin appendages and in particular the persistence of this effect. The in vivo measurement can be carried out by chromametry. This technique measures the absorbance at distinct wavelengths (OD 420/520/620 nm) and allows a measurement of three parameters (L*, a* and b*) (L* represents the "clarity", a* represents the "redness" and b* represents the "yellowness").

The decrease in the amount of melanin and/or in the pigment spots can also be measured by a Siascope® (siascopy technique), generating a high-resolution spectrophotometric intracutaneous analysis and making it possible to measure in particular the total concentration of melanin in the epidermis.

The use of the *L. domesticum* extract according to the invention is thus for decreasing the pigmentation of the skin and/or of the skin appendages, preferentially of the body hair, and/or decreasing the brown spots on the skin, advantageously in a long-lasting manner.

For the purposes of the present invention, the expression "decreasing the pigment spots on the skin" is intended to mean a decrease in the pigmentation of the localized pigment spots, in particular in the number and/or the intensity of the pigment spots, typically on the areas of the face, neckline, neck, back, shoulders and/or hands, particularly spots on the back of the hands. The pigment spots are in particular "brown spots" or "age spots" when they are located on a part of the body exposed to UV radiation and/or associated with chronological ageing or UV-induced ageing, for example during exposure to the sun. The pigment spots also include freckles, and/or post-inflammatory spots and/or spots which appear in response to attacks, and/or which are of hormonal origin, in particular in the context of a chloasma, and/or of drug-related origin, and/or for preventing and/or combating the unaesthetic pigment manifestations accompanying a pathological condition.

The *L. domesticum* extract according to the invention is a topically and/or orally acceptable cosmetic and/or nutraceutical or pharmaceutical, preferentially dermatological, extract. For the purposes of the present invention, the expression "topically and/or orally acceptable" is intended to mean an ingredient which is suitable for application, respectively, topically and/or orally, which is non-toxic and non-irritant to the skin and does not induce an allergic response, and which is not chemically unstable.

The use of the extract according to the present invention may be oral and/or topical. Advantageously, it is used topically. For the purposes of the present invention, the term "topically" is intended to mean direct local application and/or vaporization of the extract on the surface of the skin.

The extract according to the invention is a leaf extract obtained by any conventional plant extraction process known to those skilled in the art. The leaves may thus be dried and/or ground before extraction. The extraction can be carried out by maceration, by hot decoction, by ultrasonic grinding, by grinding with a mixer, by extraction under subcritical or supercritical (carbon dioxide) conditions, or else by simple stirring, preferentially with magnetic stirring. Preferentially, the extraction is carried out by maceration with magnetic stirring.

In one embodiment of the invention, the *L. domesticum* extract is obtained by extraction, preferentially by magnetic stirring, of the leaves in a solvent or a mixture of solvents, preferably a protic polar solvent, and advantageous in water, an alcohol, a glycol, a polyol, or a water/alcohol, water/glycol or water/polyol mixture (such as water mixed with ethanol, glycerol and/or butylene glycol and/or other glycols, such as xylitol, etc.) from 100/0 to 0/100 (w/w). More preferentially, the solvent used consists of water alone.

Preferentially, the extract is obtained by aqueous extraction. For the purposes of the present invention, the expression "extract obtained by aqueous extraction" is intended to mean any extract obtained by extraction with an aqueous solution containing more than 60% by weight, advantageously at least 70% by weight, in particular at least 80% by weight, more particularly at least 90% by weight, particularly at least 95% by weight, of water relative to the total weight of the aqueous solution, even more advantageously not containing glycol and in particular not containing alcohol, more particularly containing only water.

The extraction can be carried out for a period ranging from 1 hour to 20 hours, preferentially from 2 hours to 16 hours. Advantageously, the extraction is carried out for a period of 2 hours.

The extraction can be carried out at a temperature of between 0° C. and 80° C., preferentially between 0° C. and 25° C., more preferentially between 4° C. and 20° C. Even more preferentially, the extraction is carried out at ambient temperature, that is to say at 20° C. In one alternative embodiment, the extraction is carried out at a temperature between 60° C. and 80° C., advantageously at a temperature of 80° C.

The extract can moreover be obtained from an amount of dry matter of from 1% to 20%, advantageously from 2% to 15%, more advantageously from 5% to 10%, and more preferentially of 10% by weight relative to the total weight of the dry matter and of the solvent used.

The extract can be obtained in liquid or powder form. When it is obtained in powder form, it is dried, and preferentially in this case, maltodextrin is added in an amount of from 20% to 90%, advantageously from 40% to 80%, more advantageously of 75%, by weight relative to the total weight of the maltodextrin before drying and of the extract.

In one preferential embodiment of the invention, the extract is obtained with magnetic stirring starting from an amount of 10% by weight of L. domesticum leaves relative to the total weight of leaves and of solvent, in water as sole solvent, for a period of 2 hours at ambient temperature, that is to say at a temperature of 20° C. The extract thus obtained is then filtered and then maltodextrin is added in an amount such that it represents 75% by weight relative to the total weight of the extract and of the maltodextrin, under conditions described in example 1a).

In another embodiment of the invention, the extract is obtained with magnetic stirring of an amount of 15% by weight of L. domesticum leaves in water as sole solvent for a period of 2 hours at ambient temperature, that is to say at a temperature of 20° C. The extract thus obtained was filtered and then spray-dried in the presence of maltodextrin added to the medium at a final concentration of 75% by weight relative to the total weight of the maltodextrin and of the extract, under the conditions described in example 1b).

In a 3rd embodiment of the invention, the extract is obtained with magnetic stirring of an amount of 10% by weight of L. domesticum leaves in a water/ethanol mixture (75, 25) (w/w) for a period of 2 hours at ambient temperature, that is to say at a temperature of 20° C. The extract thus obtained was filtered and then spray-dried in the presence of maltodextrin added to the medium at a final concentration of 75% by weight relative to the total weight of the maltodextrin and of the extract, under conditions described in example 1c).

In yet another embodiment of the invention, the extract is obtained with magnetic stirring of an amount of 10% by weight of L. domesticum leaves in water as sole solvent, for a period of 2 hours at a temperature of 80° C. The extract thus obtained was filtered and then spray-dried in the presence of maltodextrin added to the medium at a final concentration of 75% by weight relative to the total weight of the maltodextrin and of the extract, under conditions described in example 1d). Advantageously, the L. domesticum leaf extract according to the invention does not contain any vitamin C or any one of the derivatives thereof.

The L. domesticum extract according to the invention can be used alone in the form of a cosmetic or nutraceutical active ingredient or else in a cosmetic or nutraceutical composition. When it is used alone in the form of an active ingredient, the extract according to the invention is preferentially soluble and dissolved in a solvent, in particular a polar solvent, such as water, an alcohol, a polyol, a glycol, or a mixture thereof, in the presence or absence of glycerin. Preferentially, the extract is dissolved in water as sole solvent for producing an easily formulatable cosmetic ingredient, as described in example 6.

Another subject of the invention thus also relates to the use of the L. domesticum extract in a cosmetic and/or nutraceutical composition also comprising at least one cosmetically and/or nutraceutically acceptable excipient. In one embodiment of the invention, the extract is present in the cosmetic composition at a concentration of from $1 \times 10^{-4}$% to 10% by weight, preferably between $1 \times 10^{-4}$% and 5% by weight, even more preferentially between $1 \times 10^{-3}$% and 3% by weight relative to the total weight of the composition, particularly between 0.001% and 0.1% by weight relative to the total weight of the composition. The term "cosmetic composition" is intended to mean herein a non-pharmaceutical composition, that is to say a composition intended for non-therapeutic use. Advantageously, the cosmetic composition is thus used for decreasing the pigmentation of the skin and/or of the skin appendages, preferentially of the body hair, and/or for decreasing the pigment spots on the skin, in particular by increasing the expression of miRNA490 and/or by decreasing the amount of tyrosinase protein, preferentially in the melanocytes.

The cosmetic composition can also comprise at least one cosmetically acceptable excipient. Advantageously, said excipient(s) is (are) chosen from at least one of the groups consisting of preserving agents, emollients, emulsifiers, surfactants, moisturizing agents, thickeners, texturing agents, film-forming agents, pigments, stabilizers, solubilizing agents, dyes and fragrances.

More advantageously, the excipient(s) is (are) chosen from the group consisting of amino acids and derivatives thereof, polyglycerols, esters, polymers and cellulose derivatives, lanolin derivatives, phospholipids, lactoferrins, lactoperoxidases, sucrose-based stabilizing agents, vitamin E and derivatives thereof, xanthan gums, natural and synthetic waxes, plant oils, triglycerides, unsaponifiables, phytosterols, plant esters, silicones and derivatives thereof, protein hydrolysates, jojoba oil and derivatives thereof, liposoluble/water-soluble esters, betaines, aminoxides, plant extracts, saccharose esters, titanium dioxides, glycines, and parabens, and more preferably from the group consisting of steareth-2, steareth-21, glycol-15 stearyl ether, cetearyl alcohol, phenoxyethanol, methylparaben, ethylparaben, propylparaben, butylparaben, butylene glycol, caprylyl glycol, natural tocopherols, glycerin, dihydroxycetyl sodium phosphate, isopropyl hydroxycetyl ether, glycol stearate, triisononanoin, octyl cocoate, polyacrylamide, isoparaffin, laureth-7, a carbomer, propylene glycol, hexylene glycol, glycerol, bisabolol, a dimethicone, sodium hydroxide, PEG 30-dipolyhydroxystearate, capric/caprylic triglycerides, cetearyl octanoate, dibutyl adipate, grapeseed oil, jojoba oil, magnesium sulfate, EDTA, a cyclomethicone, xanthan gum, citric acid, sodium lauryl sulfate, mineral oils and waxes, isostearyl isostearate, propylene glycol dipelargonate, propylene glycol isostearate, PEG 8, beeswax, hydrogenated palm kernel oil glycerides, lanolin oil, sesame oil, cetyl lactate, lanolin alcohol, castor oil, titanium dioxide, lactose, saccharose, low-density polyethylene, and an isotonic saline solution.

The composition of the invention can be chosen from an aqueous or oily solution, a cream or an aqueous gel or an oily gel, in particular a shower gel, a milk, an emulsion, a microemulsion or a nanoemulsion, which is in particular oil-in-water or water-in-oil or multiple or silicone-based, a mask, a serum, a lotion, a liquid soap, a dermatological bar, an ointment, a foam, a patch, an anhydrous product, which is preferably liquid, pasty or solid. Preferentially, the cosmetic composition according to the invention is a cream or a serum.

Advantageously, the cosmetic composition according to the invention is intended to be applied, advantageously topically, to all or part of the body chosen from the hands, the neck, the neckline, the stomach, the arms, the thighs, the hips, the waist, and/or the face and/or the skin appendages, and preferentially the hands, the neck, the neckline and the face, more preferentially the face.

In another embodiment of the invention, the *L. domesticum* extract according to the invention is included in a nutraceutical composition also comprising at least one nutraceutically acceptable excipient, at a concentration of from $1 \times 10^{-4}\%$ to 10% by weight, preferentially between $1 \times 10^{-4}\%$ and 5% by weight, more preferentially between $1 \times 10^{-3}\%$ and 3% by weight relative to the total weight of the composition, particularly between 0.001% and 0.1% by weight relative to the total weight of the composition. The term "nutraceutical composition" is intended to mean a composition which can be administered orally as a non-therapeutic food supplement and which is in the form of gel capsules, capsules, a powder or a gel. It is not therefore a medicament.

The cosmetic and/or nutraceutical composition of the present invention can contain one or more other cosmetic and/or nutraceutical active ingredients, resulting in a supplementary effect and/or an effect of synergy with the extract according to the invention.

Thus, the composition according to the invention may contain one or more other depigmenting and/or lightening active agents and/or active agents intended for decreasing the pigment spots on the skin, such as niacinamide or vitamin B3, arbutin, azeleic acid, ascorbic acid or derivatives thereof, a combination of the *Saxifrage sarmentosa, Psidium guajava* and *Carica papaya* plant extracts sold by BASF Beauty Care Solutions France under the name Dermawhite™ WF, a combination of sulfites and *Camellia sinensis, Scutellaria baicalensis, Cucumis sativus* and *Pyrus malus* extracts, sold under the name Phytolight™ BG or a combination of a pea extract and of sucrose dilaurate sold under the name Actiwhite™, or else 4-hydroxyphenoxyacetic acid derivatives, in particular 2-(4-hydroxyphenoxy) propionic acid sold under the name Radianskin™ by BASF Beauty Care Solutions France.

Among other active ingredients which may be combined with the extract according to the invention, mention will be made of "anti-ageing" active agents such as:

an agent which stimulates fibronectin synthesis, in particular a maize extract, such an extract being in particular sold by BASF Beauty Care Solutions France under the name Deliner™ and the palmitoyl pentapeptide sold by the company Sederma under the tradename Matrixil®;

an agent which stimulates the formation of elastic fibres, such as an *Origanum majorana* extract sold under the name Dermagenist™ by the applicant;

an agent which stimulates the expression of perlecan and of dystroglycan in the extracellular matrix and/or in the epithelial basal membrane, for instance a *Polygonum bistorta* extract sold under the name Perlaura™ by BASF Beauty Care Solutions France;

an agent for protecting extracellular matrix fibroblast growth factor (FGF2) against degradation thereof and/or denaturation thereof, in particular a *Hibiscus abelmoscus* extract as described in the patent application in the name of BASF Beauty Care Solutions France filed under number FR0654316 and sold by BASF Beauty Care Solutions France under the name Linefactor™ and/or an agent for stimulating fibroblast growth, for example a fermented soya extract containing peptides, known under the name Phytokine™ sold by BASF Beauty Care Solutions France and also described in patent application EP 1 119 344 B1 (Laboratoires Expanscience), and preferentially a combination of these two extracts;

an agent which stimulates laminin synthesis, in particular a biotechnology-modified malt extract, such an extract being in particular sold by BASF Beauty Care Solutions France under the name Basaline™;

an agent which stimulates hyaluronan synthase 2 (HAS2) expression and/or activity, such as the plant extracts described in patent application FR 2 893 252 A1 and in particular an aqueous extract of Galanga (*Alpinia galanga*) and sold by BASF Beauty Care Solutions France under the name Hyalufix™;

an agent which stimulates lysyl oxidase like (LOXL) synthesis, such as a *Geophila cordifolia* extract and those described in patent application FR 2 855 968, and in particular a dill extract sold by BASF Beauty Care Solutions France under the name Lys'Lastine™;

an agent which stimulates intracellular ATP synthesis, in particular an extract of the alga *Laminaria digitata;* a collagen-stimulating active agent such as retinal and/or vitamin C;

an active agent which inhibits metalloproteinases (MMPs) such as more particularly MMPs 1, 2, 3, 9, such as retinoids and derivatives, oligopeptides and lipopeptides, lipoamino acids, the *Argania spinosa* leaf extract sold by BASF Beauty Care Solutions France SAS under the name Arganyl™; lycopene; isoflavones, quercetin, kaempferol, apigenin;

a replumping agent, in particular the hyaluronic acid filling spheres sold by BASF Beauty Care Solutions France under the name Hyaluronic Filling Spheres™;

an agent for increasing the expression of LOX for augmenting the architecture of the epidermis, for instance a *Cichorium intybus* extract sold under the name LOX-Age™ by BASF Beauty Care Solutions France;

an agent for increasing collagen deglycation and/or increasing the expression of type I collagen, such as a combination of a *Salvia miltiorrhiza* leaf extract and of niacin, sold by BASF Beauty Care Solutions France under the name CollRepair™;

an agent which stimulates lumican and collagen synthesis, such as a synthetic acetyl Gln Asp Val His tetrapeptide sold by BASF Beauty Care Solutions France under the name Dermican™ and described in patent application WO 2005/120554 A1;

an agent for protecting and stimulating elastin and collagen, such as the *Manilkara multinervis* leaf extract sold by BASF Beauty Care Solutions France under the name Elestan™ and the *Eperua falcata* root extract sold by BASF Beauty Care Solutions France under the name Eperuline™;

agents which stimulate keratinocyte proliferation, which preferentially can be used in the composition according to the invention, in particular retinoids such as retinol and esters thereof, including retinyl palmitate, and phloroglucinol;

agents which stimulate keratinocyte differentiation, for example minerals such as calcium and lignans such as secoisolariciresinol, and also the *Achillea millefollium* extract sold under the name Neurobiox™ by BASF Beauty Care Solutions France.

The cosmetic and/or nutraceutical composition may also contain one or more anti-ageing active ingredients. Thus, the *L. domesticum* extract according to the invention may be combined with a dill extract sold under the name Lys'Lastine™ by BASF Beauty Care Solutions France, a *Polygonum* bistorta extract sold under the name Perlaura™, an *Origanum majorana* extract sold under the name Dermagenist™, an argan pulp extract sold under the name Argassential™ or a *Cichorium intybus* extract sold under the name LOX-Age™, a *Manilkara multinervis* leaf extract sold by BASF Beauty Care Solutions France under the name Elestan™, an *Eperua falcata* root extract sold by BASF Beauty Care Solutions France under the name Eperuline™ or else an argan oil extract sold under the name Arganyl™ by BASF Beauty Care Solutions France.

As soothing agents which are part of the composition of the invention, use may be made of pentacyclic triterpenes, ursolic acid and salts thereof, oleanolic acid and salts thereof, betulinic acid and salts thereof, salicylic acid salts and in particular zinc salicylate, bisabolol, allantoin, omega-3 unsaturated oils, cortisone, hydrocortisone, indomethacin and betamethasone, anti-inflammatory active agents, and in particular those described in application FR 2 847 267, in particular the *Pueraria lobata* root extract sold under the name Inhipase™ by the applicant, *Theobroma cacao* extracts. The vasoprotector or vasodilator active ingredients which act on the microcirculation can be chosen from flavonoids, ruscogenins, nicotinates and essential oils.

Another subject of the invention relates to a cosmetic care process comprising the topical application of the *L. domesticum* extract according to the invention or of the cosmetic composition comprising same, for decreasing the pigmentation of the skin and/or of the skin appendages, preferentially of the body hair, and/or decreasing the pigment spots on the skin, in particular by increasing the expression of miRNA490 and/or by decreasing the amount of tyrosinase protein, preferentially in the melanocytes.

In one embodiment of the invention, the cosmetic care process comprises the topical application of the extract according to the invention or of the cosmetic composition comprising same to all or part of the body chosen from the hands, the neck, the neckline, the stomach, the arms, the thighs, the hips, the waist and/or the face, and/or the skin appendages, and preferentially the hands, the neck, the neckline and/or the face, more preferentially the face.

The process according to the invention thus consists of the application, preferentially topically, of a cosmetic composition comprising the *L. domesticum* extract according to the invention at a concentration of from $1\times10^{-4}$% to 10% by weight, preferentially between $1\times10^{-4}$% and 5% by weight, more preferentially between $1\times10^{-3}$% and 3% by weight relative to the total weight of the composition, particularly between 0.001% and 0.1% by weight relative to the total weight of the composition. Advantageously, the composition is applied at least once per day, preferentially twice per day, for a period of 30 days, preferentially 56 days.

Yet another subject of the present invention relates to the *L. domesticum* extract according to the invention, for the pharmaceutical, preferentially dermatological, use thereof, preferentially topically, in the treatment of pathological conditions involving a pigment dysregulation, such as Addison's disease, liver failure, purpura, a melanoma or dermatosis papulosa nigra, which is described as pathological hyperpigmentation. In one embodiment of the invention, the extract is present in a pharmaceutical, preferentially dermatological, composition also comprising at least one pharmaceutically, preferentially dermatologically, acceptable excipient, at a concentration by weight of from $1\times10^{-4}$% to 10%, preferentially between $1\times10^{-4}$% and 5%, more preferentially between $1\times10^{-3}$% and 3% by weight relative to the total weight of the composition, particularly between 0.001% and 0.1% by weight relative to the total weight of the composition.

Examples making reference to the description of the invention are presented hereinafter. These examples are given by way of illustration and could not in any way limit the scope of the invention. Each of the examples has a general scope. Furthermore, in the examples, all the percentages are given by weight, unless otherwise indicated, the temperature is expressed in degree(s) Celsius unless otherwise indicated, and the pressure is atmospheric pressure, unless otherwise indicated.

The examples are an integral part of the present invention and any feature which appears to be novel with respect to any prior art on the basis of the description taken as a whole, including the examples, is an integral part of the invention.

EXAMPLES

Example 1: Various Methods for Preparing the *Lansium domesticum* Extract

Example 1a

Ten percent (10%) by weight of *L. domesticum* leaves were extracted with magnetic stirring in water as sole solvent for a period of 2 hours at ambient temperature, that is to say at a temperature of 20° C. The extract thus obtained was filtered and then spray-dried in the presence of maltodextrin added to the medium at a final concentration of 75% by weight relative to the total weight of the maltodextrin and of the extract (w/w). The extract thus obtained is in powder form.

Example 1b

Fifteen percent (15%) by weight of *L. domesticum* leaves were extracted with magnetic stirring in water as sole solvent for a period of 2 hours at ambient temperature, that is to say at a temperature of 20° C. The extract thus obtained was filtered and then spray-dried in the presence of maltodextrin added to the medium at a final concentration of 75% by weight relative to the total weight of the maltodextrin and of the extract (w/w). The extract thus obtained is in powder form.

Example 1c

Ten percent (10%) by weight of *L. domesticum* leaves were extracted with magnetic stirring in a water/ethanol mixture (75, 25) (w/w) for a period of 2 hours at ambient temperature, that is to say at a temperature of 20° C. The extract thus obtained was filtered and then spray-dried in the presence of maltodextrin added to the medium at a final concentration of 75% by weight relative to the total weight of the maltodextrin and of the extract (w/w). The extract thus obtained is in powder form.

Example 1d

Ten percent (10%) by weight of *L. domesticum* leaves were extracted with magnetic stirring in water as sole solvent for a period of 2 hours at a temperature of 80° C. The extract thus obtained was filtered and then spray-dried in the presence of maltodextrin added to the medium at a final concentration of 75% by weight relative to the total weight of the maltodextrin and of the extract (w/w). The extract thus obtained is in powder form.

Example 2: Decrease in the Amount of Tyrosinase (TYR) Protein in the Presence of miRNA490

Protocol:

Normal human melanocytes, that is to say not exhibiting any pathological skin condition, from a normal healthy donor, were cultured in an M-PRO specific medium containing K-SFM (Invitrogen) with geniticin (100 µg/ml) and normocin (0.3%), with or without addition of synthetic miRNA490 (20 nmol/l final concentration). The cells were cultured at 37° C. (under 5% $CO_2$) and then seeded into an M-DIF medium for the extraction below.

The total cell proteins were extracted from the melanocytes cultured above, with a lysis buffer (RIPA, Sigma) supplemented with an anti-protease cocktail (Roche). An amount of 13 µg of proteins of each sample was purified on gel (NuPage Novex, Invitrogen) then transferred onto a cellulose membrane. The membranes were saturated with a Tris buffer (5% Tris buffered saline) for 1 hour at ambient temperature and then incubated at 4° C. overnight with an anti-TYR (sc-20035) and anti-TRP1 (sc-58438) primary antibody or an anti-actin (HRP-b-actin (A3854)) primary antibody (Sigma) as control, followed by a second incubation for 1 hour at ambient temperature with a secondary antibody. The detection was carried out with the ECL prime kit (GE Amersham). The amount of tyrosinase (TYR) was measured by Western blot, the results are presented below and are the mean (MEAN) of three assays (n=3).

Results:

TABLE 2

|  | MEAN | SD |
|---|---|---|
| Control | 100 | 1.0 |
| +miRNA490 (20 nmol/l) | 53.5 | 7.4 |

SD: Standard deviation;
MEAN: mean
Conclusion: these results showed that miRNA490 caused a decrease of at least 46.5% of the amount of tyrosinase detected in the human melanocytes.

Example 3: Decrease in the Amount of Tyrosinase (TYR) Protein in the Presence of the *Lansium domesticum* Extract Protocol:

Normal human melanocytes were cultured in an M254 culture medium (Life technologies) at a temperature of 37° C. (5% $CO_2$), then the *L. domesticum* extract prepared according to example 1a) was added to the medium at a final concentration of $8.5 \times 10^{-3}$% (volume/volume). The cells were lysed and the amount of total protein was measured by the BSA method.

The amount of protein was measured by Western blot (Sally Sue, Protein Sample, San Jose) (n=6).

Results:

TABLE 3

|  | MEAN |
|---|---|
| Control | 100 |
| *L. domesticum* extract $8.5 \times 10^{-3}$ % (v/v) | 63.11 |

(n = 6; p < 0.01 (**))
SD: Standard deviation;
MEAN: mean

The *L. domesticum* extract according to the invention made it possible to decrease the amount of tyrosinase by at least 37%.

Example 4: Increase in the Expression of miRNA490 in Normal Human Melanocytes in the Presence of the *Lansium domesticum* Extract Protocol:

The culturing of the melanocytes was carried out as described in the protocol of example 2. The total RNA was extracted from the melanocytes after culture (SV 96 total RNA Isolation System kit) then converted into cDNA by RT-PCR (mi SCRIPT SYBR Green PCR kit). The amplification of the miRNA490 (Table 4) was carried out using the commercial primers (Qiagen) (references 218300 MS00004319 (Hs_miR-490_1 miScript Primer Assay) and QF00065247 (Hs_RNU1-8_QF_1 QuantiFast Probe Assay) for the reference gene (Accession number NR_004430.2)).

TABLE 4

| | Sequence |
|---|---|
| miR-490-3p (MIMAT0002806 (mirBase)) | CAACCUGGAGGACUCCAUGCUG SEQ ID No 2 |

Results:

The results presented in Table 5 are the mean of five assays (n=5)

TABLE 5

|  | MEAN | SD |
|---|---|---|
| Control | 100 | 15.0 |
| *L. domesticum* extract at $9 \times 10^{-3}$ (w/w) | 143.2 | 26.8 |

SD: Standard deviation;
MEAN: mean
Conclusion: the *L. domesticum* extract according to the invention made it possible to increase the expression of miRNA490 in the human melanocytes by at least 1% and up to 85%.

Example 5: Decrease in the Amount of Melanin in the Presence of the *Lansium domesticum* Extract Protocol:

B16 melanocytes were cultured in Eagle's Minimum Essential Medium containing 2% foetal serum (foetal calf serum) for 3 days at 37° C. under 5% $CO_2$, then the *L. domesticum* extract was added at a final concentration of $4 \times 10^{-3}$ or $9 \times 10^{-3}$ by weight relative to the total weight of the medium (w/w) and the medium was incubated for a further three days. The same medium was incubated under identical conditions without *L. domesticum* extract in the presence of NDP-a-MSH (control). The amount of melanin was measured by measuring the optical density at 475 nm.

The results of the melanin measurement are the mean of six assays (n=6).
Results:

TABLE 6

|  | MEAN | SD |
|---|---|---|
| Control | 100 | 6 |
| *L. domesticum* extract $4 \times 10^{-3}$ % (w/w) | 19.2 | 1.7 |
| *L. domesticum* extract $9 \times 10^{-3}$ % (w/w) | 21.4 | 0.6 |

SD: Standard deviation;
MEAN: mean
Conclusion: the results showed a decrease of at least 78% of the amount of melanin detected in the melanocytes and up to 88.5%, in the presence of the *L. domesticum* extract according to the invention.

Example 6: Cosmetic Ingredient Comprising a *Lansium domesticum* Extract

| *L. domesticum* extract according to example 1a) | 0.1-10% |
|---|---|
| Water | qs 100 |

Example 7: Cosmetic Compositions Comprising the Active Ingredient According to the Invention The compositions below are prepared according to methods known to those skilled in the art, in particular as regards the various phases to be mixed together. *The cosmetic ingredient corresponds to that of example 6 above.

Formulation 7a:

| Cosmetic ingredient* | 0.001-10% |
|---|---|
| EDTA | 0.05 |
| Steareth-2 | 2.00 |
| Steareth-21 | 2.50 |
| Cetearyl alcohol | 1.00 |
| Propylheptyl caprylate | 15.00 |
| Sodium hydroxide (30% in solution) | 0.10 |
| Mixture of phenoxyethanol, chlorphenesin, benzoic acid, butylene glycol, sorbic acid (Germazide ™ PBS) | 1.25 |
| Mixture of polyacrylate-X, isohexadecane and polysorbate 60 (Sepigel ™ SMS 60) | 4.00 |
| Water | qs 100 |

Formulation 7b:

Use of the cosmetic ingredient according to the invention in a formulation of water-in-oil type

| A | PEG 30 Dipolyhydroxystearate | 3 |
|---|---|---|
|   | Captic triglycerides | 3 |
|   | Cetearyl octanoate | 4 |
|   | Dibutyl adipate | 3 |
|   | Grapeseed oil | 1.5 |
|   | Jojoba oil | 1.5 |
|   | Phenoxyethanol, methylparaben, propylparaben, butylparaben, ethylparaben | 0.5 |
| B | Glycerin | 3 |
|   | Butylene glycol | 3 |
|   | Magnesium sulfate | 0.5 |
|   | EDTA | 0.05 |
|   | Water | qs 100 |
| C | Cyclomethicone | 1 |
|   | Dimethicone | 1 |
| D | Fragrance | 0.3 |
| E | Cosmetic ingredient* | 0.001-10% |

Formulation 7c:

Use of the products of the invention in an aqueous gel formulation (face)

| A | Water | qs 100 |
|---|---|---|
|   | Carbomer | 0.5 |
|   | Butylene glycol | 15 |
|   | Phenoxyethanol, methylparaben, propylparaben, butylparaben, ethylparaben | 0.5 |
| B | Cosmetic ingredient* | 0.001-10% |

Formulation 7d:

Use of the products of the invention in a formulation of shampoo or shower gel type (body)

| A | Water | qs 100 |
|---|---|---|
| B | Butylene glycol, methylparaben, Ethylparaben, propylparaben | 0.5 |
|   | Phenoxyethanol, methylparaben, propylparaben, butylparaben, ethylparaben | 0.5 |
| C | Citric acid | 0.8 |
| D | Sodium Laureth Sulfate | 40.0 |
| E | Cosmetic ingredient* | 0.001-10% |

Example 8: Example of Cosmetic Formulation Containing the Extract According to the Invention Intended for Face Care

| | | |
|---|---|---|
| A | Glyceryl Stearate, Ceteareth-20, Ceteareth-12, Cetearyl Alcohol, Cetyl Palmitate | 6.00 |
| | Cetearyl Alcohol | 2.00 |
| | Cetearyl Isononanoate | 3.00 |
| | Isopropyl Myristate | 5.00 |
| | Propylheptyl caprylate | 2.00 |
| | Dicaprylyl Carbonate | 2.00 |
| | Dimethicone | 1.00 |
| | Tocopherol | 0.20 |
| B | Water | 67.25% |
| | Propylene Glycol, Phenoxyethanol, Chlorphenesin, Methylparaben | 2.50 |
| | Disodium EDTA | 0.05 |
| | Butylene Glycol | 3.00 |
| C | Xanthan gum | 0.2 |
| | Sodium stearoyl glutamate | 0.5 |
| D | Water | 5 |
| | Extract according to example 1a) | 0.3% |

Example 9: In Vivo Analysis of the Decrease in the Amount of Melanin and in the Surface Area of the Pigment Spots on the Skin in the Presence of an *L. domesticum* Extract Protocol:

the decrease in amount of melanin and in the surface area of the pigment spots was evaluated by means of the siascopy technique (Siascope®) on the facial skin of a population of 25 women from 18 to 70 years old, of Asian origin (Phototype III, IV), having a non-uniform coloration of the skin and pigment spots.

The application of the cosmetic formulation of example 8, containing 0.3% by weight of the *L. domesticum* extract prepared according to example 1a), relative to the total weight of the formulation, or of the same formulation without extract, termed placebo, was carried out on the half-faces of the population for a period of 56 days. The results are presented on base 100 (T0) and correspond to a percentage decrease after 56 days of application.

Result:

TABLE 7

Decrease in the surface area of the pigment spots (%)

| | T0 | T56 | T56/T0 |
|---|---|---|---|
| Placebo | 100 | 95 | −5 |
| *L. domesticum* extract Ex. 1a) 0.3% | 100 | 77 | −23** |

(Student's test: **p < 0.01)

Conclusion: the *L. domesticum* extract decreased the surface area of the pigment spots by 23% after 56 days of application, and by 18% in comparison with the placebo.

TABLE 8

Decrease in the amount of melanin (%)

| | T0 | T56 | T56/T0 |
|---|---|---|---|
| Placebo | 100 | 83 | −7 |
| *L. domesticum* extract Ex. 1a) 0.3% | 100 | 77 | −23** |

(Student's test: **p < 0.01) Conclusion: the *L. domesticum* extract decreased the amount of melanin by 23% after 56 days of application, and by 16% in comparison with the placebo.

The invention claimed is:

1. A method for decreasing pigmentation of skin or skin appendages, and/or for decreasing pigment spots on skin, comprising administering an effective amount of a *Lansium domesticum* leaf extract or a composition comprising said *Lansium domesticum* leaf extract to a human subject in need thereof.

2. The method of claim 1, wherein the *Lansium domesticum* leaf extract is obtained by extraction in water, alcohol, glycol, polyol, or a mixture of water/alcohol, water/glycol or water/polyol of 100/0 to 0/100 (w/w).

3. The method of claim 1, wherein the *Lansium domesticum* leaf extract is obtained by aqueous extraction.

4. The method of claim 1, wherein the *Lansium domesticum* leaf extract is present in a cosmetic composition comprising at least one cosmetically acceptable excipient, wherein the *Lansium domesticum* leaf extract is at a concentration of from $1\times10^{-4}$% to 10% by weight, between $1\times10^{-4}$% and 5% by weight, between $1\times10^{-3}$% and 3% by weight, or between 0.001% and 0.1% by weight relative to the total weight of the composition.

5. The method of claim 1, wherein the *Lansium domesticum* leaf extract is present in a nutraceutical composition comprising at least one nutraceutically acceptable excipient, wherein the *Lansium domesticum* leaf extract is at a concentration of from $1\times10^{-4}$% to 10% by weight, between $1\times10^{-4}$% and 5% by weight, between $1\times10^{-3}$% and 3% by weight, or between 0.001% and 0.1% by weight relative to the total weight of the composition.

6. The method of claim 1, wherein the *Lansium domesticum* leaf extract increases the expression of miRNA490 and/or decreases the amount of tyrosinase protein in skin or skin appendages of the human subject.

7. The method of claim 1, wherein the *Lansium domesticum* leaf extract increases the expression of miRNA490 and/or decreases the amount of tyrosinase protein in melanocytes of the human subject.

8. The method of claim 1, wherein the *Lansium domesticum* leaf extract or the composition comprising said *Lansium domesticum* leaf extract is administered topically onto skin or skin appendages of said human subject.

9. The method of claim 1, wherein the *Lansium domesticum* leaf extract or the composition comprising said *Lansium domesticum* leaf extract is topically applied onto all or part of a human body selected from the group consisting of hand, neck, neckline, stomach, arm, thigh, hip, waist, and face.

10. The method of claim 1, wherein the *Lansium domesticum* leaf extract or the composition comprising said *Lansium domesticum* leaf extract is administered orally.

11. The method of claim 1, wherein the *Lansium domesticum* leaf extract is in a nutraceutical composition in form of gel capsules, capsules, powder, or gel.

12. A method for treating a pathological condition including pigment dysregulation, comprising administering an effective amount of a *Lansium domesticum* leaf extract to a human subject in need thereof.

13. The method of claim 12, wherein the pathological condition is a pathological hyperpigmentation.

14. The method of claim 12, wherein the pathological condition is Addison's disease, liver failure, purpura, melanoma, or dermatosis papulosa nigra.

15. The method of claim 12, wherein the *Lansium domesticum* leaf extract is obtained by extraction in water, alcohol, glycol, polyol, or a mixture of water/alcohol, water/glycol or water/polyol of 100/0 to 0/100 (w/w).

16. The method of claim 12, wherein the *Lansium domesticum* leaf extract is obtained by aqueous extraction.

17. The method of claim 12, wherein the *Lansium domesticum* leaf extract increases the expression of miRNA490 and/or decreases the amount of tyrosinase protein in melanocytes of the human subject.

18. The method of claim 12, wherein the *Lansium domesticum* leaf extract is administered topically.

19. The method of claim 12, wherein the *Lansium domesticum* leaf extract is present in a pharmaceutical or dermatological composition comprising at least one pharmaceutically or dermatologically acceptable excipient, wherein the *Lansium domesticum* leaf extract is at a concentration of from $1\times10^{-4}$% to 10% by weight, between $1\times10^{-4}$% and 5% by weight, between $1\times10^{-3}$% and 3% by weight, or between 0.001% and 0.1% by weight relative to the total weight of the composition.

20. A pharmaceutical or dermatological composition comprising a *Lansium domesticum* leaf extract and a pharmaceutically or dermatologically acceptable excipient, wherein said *Lansium domesticum* leaf extract is present at a concentration of from $1\times10^{-4}$% to 10% by weight, between $1\times10^{-4}$% and 5% by weight, between $1\times10^{-3}$% and 3% by weight, or between 0.001% and 0.1% by weight relative to the total weight of the composition.

\* \* \* \* \*